United States Patent [19]

Fontaine

[11] 4,258,573
[45] Mar. 31, 1981

[54] IN LINE ULTRASONIC INSPECTION APPARATUS AND METHOD

[75] Inventor: Gerard O. Fontaine, Cumberland, R.I.

[73] Assignee: Checon Corporation, Attleboro, Mass.

[21] Appl. No.: 73,496

[22] Filed: Sep. 7, 1979

[51] Int. Cl.³ .............................................. G01N 29/04
[52] U.S. Cl. .................................... 73/621; 346/33 F
[58] Field of Search ................. 73/621, 620, 629, 633, 73/634; 228/104; 346/33 F

[56] References Cited

U.S. PATENT DOCUMENTS 2,836,059  5/1958  Beaujard et al. ........................ 73/620

FOREIGN PATENT DOCUMENTS 1008195  10/1965  United Kingdom .................... 346/33 F
1114835   5/1968  United Kingdom .................... 346/33 F

*Primary Examiner*—Stephen A. Kreitman

[57] ABSTRACT

Method and apparatus for in line ultrasonic inspection of linearly extending brazed composite workpiece including a linearly extending bonded region, traveling linearly at a given speed. A source of ultrasonic signals is focussed on the workpiece and is reciprocated in the plane of the workpiece in a sweep transverse to the direction of workpiece travel, the sweep being at least commensurate with the width of the bonded region. The signals reflected from the workpiece are received and processed to derive control signals, which are input to a marker. The marker is reciprocated in phase with the reciprocation of the signal source. A linearly extending record medium is moved past the marker transversely to the reciprocation of the marker at a speed not greater than one-half the workpiece speed, whereby the marker traces successive generally parallel strokes against said record medium. The resulting record gives a useful representation of the condition of the entire bonded region, allowing the bonding conditions to be correct during production.

6 Claims, 7 Drawing Figures

IN LINE ULTRASONIC INSPECTION APPARATUS AND METHOD

This invention relates to ultrasonic inspection apparatus, for use in the manufacture of continuously brazed contact strip materials and the like.

A large proportion of industrial electrical controls use brazed silver or silver-cadmium oxide contact assemblies. In recent years, because of the high cost of silver, the electrical control industry has been reducing the size of electrical contacts in many devices in order to reduce the quantity of silver used. Particularly in the manufacture of relatively small contact assemblies, one common method of manufacture is to stamp the contact from a toplay or overlay composite strip. The strip is produced by continuously brazing silver contact material onto a base material, in strip form, under conditions of heat and pressure. The strip thus formed may be several hundred feet long, and is supplied in a coil to a press which stamps out individual contacts from the strip material.

This technique is cost effective and generally reliable. However, the bond between the silver contact material and base material is a point at which failure can occur. Such contacts are employed at high current densities and steep thermal gradients, which places severe demands upon the performance characteristics of the contact materials. The quality of the bond materially influences the life of the contact, particularly during high current interruption tests. According to some estimates, the life of a contact can be reduced by as much as 50% by a poorly brazed joint.

The quality of the bond can vary greatly with the bonding conditions. To ensure the manufacture of strip material having a good bond, the bonding line operator must continuously control the feed rate of the strip, the temperature and the pressure.

It is known that ultrasonic scanning methods can accurately detect the condition of the bond in such strip materials, by revealing the presence of voids. However, until now, the use of ultrasonic scanning methods in the manufacture of continuously brazed strip contact materials has been limited to two aspects.

In the first aspect, the scanning has been used as a preliminary step, to help the operator of the bonding apparatus set the operating conditions. The operator bonds several short lengths of toplay by way of experiment, each of which is examined ultrasonically to determine what kind of bond is being made under the given conditions. An experienced operator can judge from the scan image what operating conditions should be changed. The appropriate changes are made and further experimental lengths are scanned, until the operator is satisfied. The operator then produces an entire coil of contact strip material nominally at the set conditions. The product may nevertheless vary in quality.

In the second aspect, the scanning has been used for quality control of the individual contacts. Samples of the finished contacts are examined ultrasonically as part of the final inspection operation. When used in conjunction with standard statistical techniques, ultrasonic scanning is valuable for quality control of the final product, but this use of the method does little to prevent the production of unsatisfactory material during the actual bonding operation.

It would therefore be advantageous to be able to reduce or prevent the production of unsatisfactory contacts by continuously monitoring the production of strip material, to make possible the correction of improper bonding conditions during the actual production process.

While it has long been recognized that it would be desirable to monitor the production process, satisfactory equipment for this purpose has not previously been provided. This is because of the difference between the rate of scanning the bonded strip required to detect all voids larger than a given size, and the rate at which the bonded strip is produced by the bonding equipment. This problem can be understood from a consideration of the scanning operation.

In ultrasonic scanning equipment, a transducer generates an ultrasonic signal by means of a crystal excited at its resonant frequency, typically 15 to 25 megahertz. This signal is focussed on the bonded strip to be scanned, and is reflected from internal voids in the brazed area. The reflected signal is returned to the transducer and is employed to actuate a pen or other output device to provide a visible indication of the void. It is necessary to emit the ultrasonic signals only at intervals, so that the reflected signal can be received at the transducer before the next signal is emitted.

Therefore, the ultrasonic vibrations are interrupted to provide a sequence of bursts. Each burst (or pulse) lasts about one microsecond, and the pulse frequency is typically 3000 cycles per second, depending on the acoustic properties of the workpiece and other parameters of the test system.

In order to insure positive detection of all flaws or voids above a selected minimum size, it is necessary to sweep the transducer over the workpiece at a speed slow enough that at least two pulses (and preferably three) will impinge on a flaw of the minimum size. For example, if the minimum flaw to be detected has a diameter of 0.015 inch, and the pulse rate is 3000 cycles per second, successive pulses must strike the workpiece at spacings of 0.005 inch. This requires a transducer sweep speed with respect to the workpiece of 15 inches per second, at which a minimum of two pulses will strike each flaw of greater than 0.015 inch diameter.

If the transducer is connected to a crank, driven by a crankshaft, for a reciprocating sweep path transverse to the direction of travel of the moving workpiece, the maximum sweep speed will be attained midway between the ends of the sweep at which the direction of the sweep is reversed. To insure detection of a void of the minimum length, oriented parallel with the sweep path, the maximum sweep speed at these midway points must not exceed 15 inches per second. Therefore the crankshaft speed must not expeed $$(15 \times 60)/(1 \times \pi) = 286 \text{ RPM}.$$

In one revolution of the crankshaft, the transducer makes two linear passes over the workpiece, both transverse to the direction of the travel of the workpiece. To insure detection of a void of the minimum length, oriented parallel to the direction of travel of the workpiece, the workpiece must not advance more than 0.015 inches between the two passes of the transducer. Therefore the rate of travel of the workpiece past the transducer must not exceed $$(286 \times 2 \times 0.015 \text{ inch})/(12 \text{ inches per foot} = 0.72 \text{ feet per minute}$$

However, this maximum rate of travel of the workpiece is at least ten times too slow for the economical operation of the bonding apparatus, which operates at speeds of from two to fifteen feet per minute, and typically at about ten feet per minute.

In order to scan a workpiece traveling at a rate of speed characteristic of economical operation of the brazing apparatus, one solution has been to eliminate the reciprocation of the transducer, and to scan only a single line within the brazed area, extending the length of the strip. However, the image produced by this scan cannot define the type and location of the voids, and at the best provides only a rough indication of the quality of the bond being produced. In fact, a line scan may completely miss voids which occur outside the scanned line. Hence this solution is not satisfactory.

It is therefore an object of the present invention to provide the capability of ascertaining the condition of the bond over the entire brazed area, and providing a visible indication of the brazed area in real time to allow the bonding operator to modify the bonding process conditions during actual production, all at speeds compatible with strip production speeds of up to 15 feet per minute.

According to the invention, a method of in line ultrasonic inspection of a linearly extending brazed composite workpiece including a linearly extending bonded region, traveling linearly at a given speed, comprises the steps of focussing a sequence of ultrasonic signals on the workpiece, and reciprocating the focus of the signals in the plane of the workpiece in a sweep transverse to the direction of travel of the workpiece. The sweep is at least commensurate with the width of the bonded region. Signals reflected from the workpiece are received, and are processed to derive control signals, which are input to a marker. The marker is reciprocated in phase with the reciprocation of the focus. A linearly extending record medium is moved past the marker transversely to the reciprocation of the marker at a speed not greater than one-half the workpiece given speed, whereby the marker traces successive generally parallel strokes against the record medium. Preferably, the record medium is moved past the marker at no more than one-quarter of the workpiece given speed. The workpiece given speed may be as much as ten times the record medium speed.

For in-line use with brazing apparatus producing a linearly extending brazed composite workpiece including a linearly extending bonded region, and moving linearly at a given speed, apparatus is provided comprising guide means defining a workpiece path through the apparatus. Scanning means is provided comprising a transducer for emitting ultrasonic signals toward the workpiece and focussed on the workpiece path, and for receiving reflected ultrasonic signals from the workpiece. The scanning means further comprises first reciprocating means for reciprocating the transducer in a linear sweep path in the lane of the workpiece path and transverse to the direction of motion of the workpiece.

Display means is provided comprising a linearly extending record medium, a marker, record medium advance means for advancing the record medium with respect to the marker at a speed not greater than one-half the workpiece given speed, and second reciprocating means for reciprocating the marker in the plane of the record medium and transverse to the advance of the record medium. The marker thereby moves in successive generally parallel strokes against the record medium.

The apparatus further comprises actuating means for actuating the first and second reciprocating means in synchronism, and processing means connected between the transducer and the marker for processing received reflected signals and for controlling the marker in accordance therewith to mark the record medium during successive strokes.

In preferred embodiments, the record medium advance means is connected to the actuating means and further provides record medium takeup means and intermittent drive means connected thereto, whereby the record medium advances only between successive strokes of the marker. Preferably, the record medium moves at a speed from one-fourth or one-tenth of the workpiece speed, and successive strokes of the marker on the record medium are spaced apart by no more than about 0.025 inch.

Other objects, features and advantages will appear from the following description of a preferred embodiment of the invention, taken together with the attached drawings thereof, in which.

Figure 1:
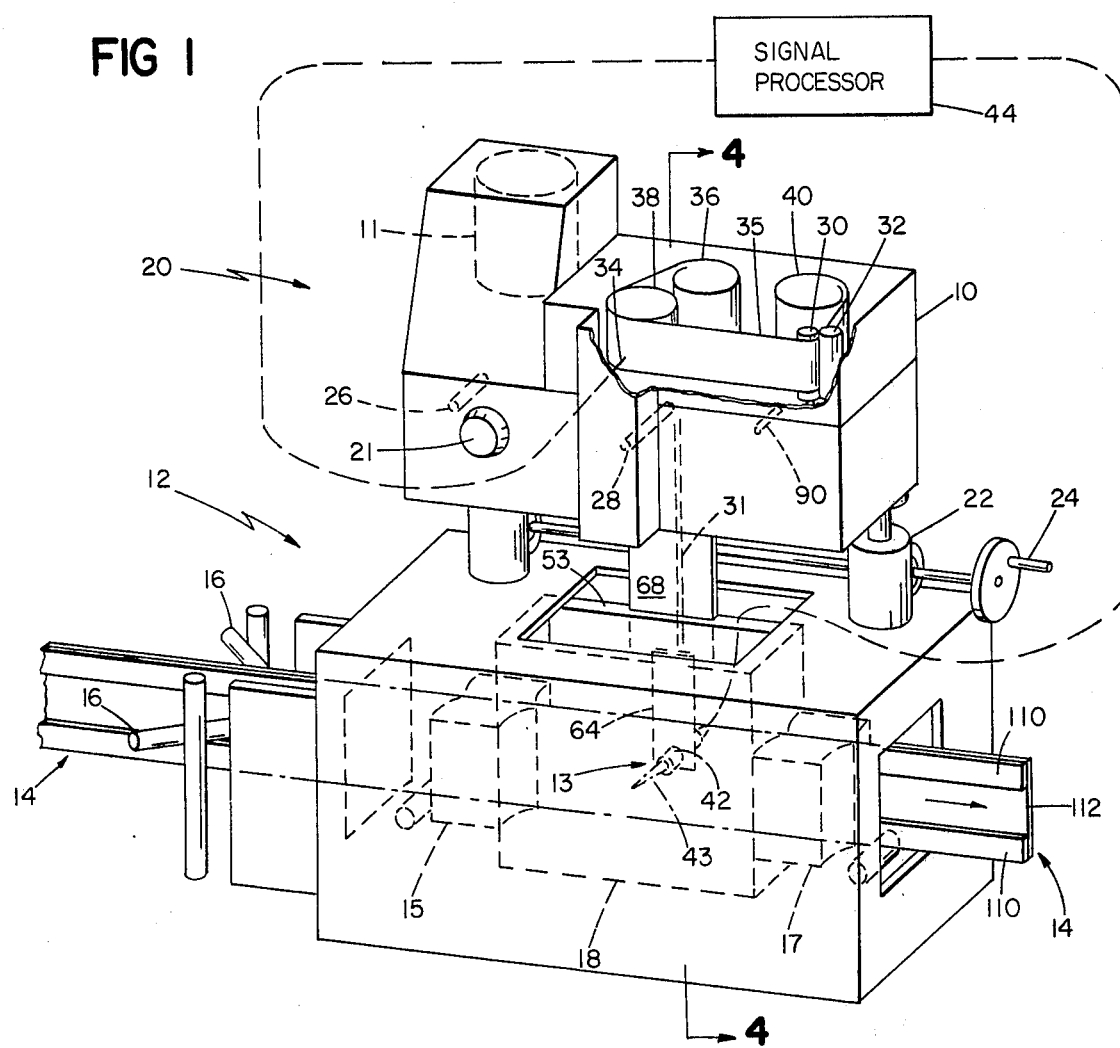
FIG. 1 is a simplified illustrative view of the apparatus of the invention, with portions indicated in phantom.

Referring now to the drawings, and particularly to FIG. 1, the scanning apparatus of the invention comprises generally an upper housing 20 disposed above a tank housing 12. The workpiece 14 to be scanned, comprising two strips of silver 110 brazed to a base strip 112, enters tank housing 12 directly from the brazing apparatus (not shown). Each silver strip 110 is about one inch wide. The scanning apparatus is preferably mounted as close to the brazing apparatus as possible, allowing a small space in which workpiece 14 is cooled. Two nozzles 16 direct sprays of water against workpiece 14 to cool it. Workpiece 14 then enters the first stuffing box 15 and then passes through water tank 18, the workpiece being completely submerged. Workpiece 14 exists through a second stuffing box 17 to suitable takeup means (not shown).

Upper housing 20 is supported on tank housing 12 by means of a jack 22; the vertical position of upper housing 20 with respect to tank housing 12 can be altered by means of jack handle 24. This permits silver strips positioned at different locations on workpiece 14 to be scanned, as will be explained.

Upper housing 20 contains a printer (recording) unit 10 and a motor 11. The speed of motor 11 is controlled conventionally by means of knob 21. Motor 11 turns a drive shaft 26 which drives a crank shaft 28 and a pair of pinch rolls 30, 32. Crank shaft 28 reciprocates a recording pen 34 in a sweep path oriented vertically as seen in FIG. 1.

A paper recording strip 35 is supplied from supply roll 36, and passes between drum 38 and pen 34 to the pair of pinch rolls 30, 32, which feed strip 35 onto takeup roll 40. The advance of paper strip 35 is not continuous, but rather intermittent, and is controlled by means to be described to be in phase with the reciprocation of pen 34 in such a way that each pen stroke is made while the paper is at rest; the strip is advanced before the next pen stroke (up or down).

A scan unit 13 is suspended at the rear of tank housing 12 from a connecting rod 31, which is connected to crank shaft 28. Scan unit 13 is thereby reciprocated in a suitable track (not shown in FIG. 1) behind water tank 18, moving in a vertically oriented linear sweep path in synchronism with the reciprocation of pen 34. Scan unit 13 provides a transducer 42 which generates short bursts of ultrasonic vibrations. Suitable focussing means (not shown) are employed to focus the ultrasonic vibrations on the path of workpiece 14, as indicated at 43. The frequency of the ultrasonic vibration is typically 15 to 25 megahertz. Each burst of energy is referred to as a pulse; each pulse lasts about one microsecond and successive pulses are emitted at a frequency of about 3000 cycles per second.

The signals reflected back from workpiece 14 are received by transducer 42 and are transmitted to a signal processor 44, which suitably modifies the signals and employs them to actuate pen 34 in accordance therewith to mark paper strip 35, to provide a visible display of the pattern of reflected signals. The design and operator of such a transducer and signal processor are well known in the art and form no part of the present invention, and will not be described herein.

Figure 3:
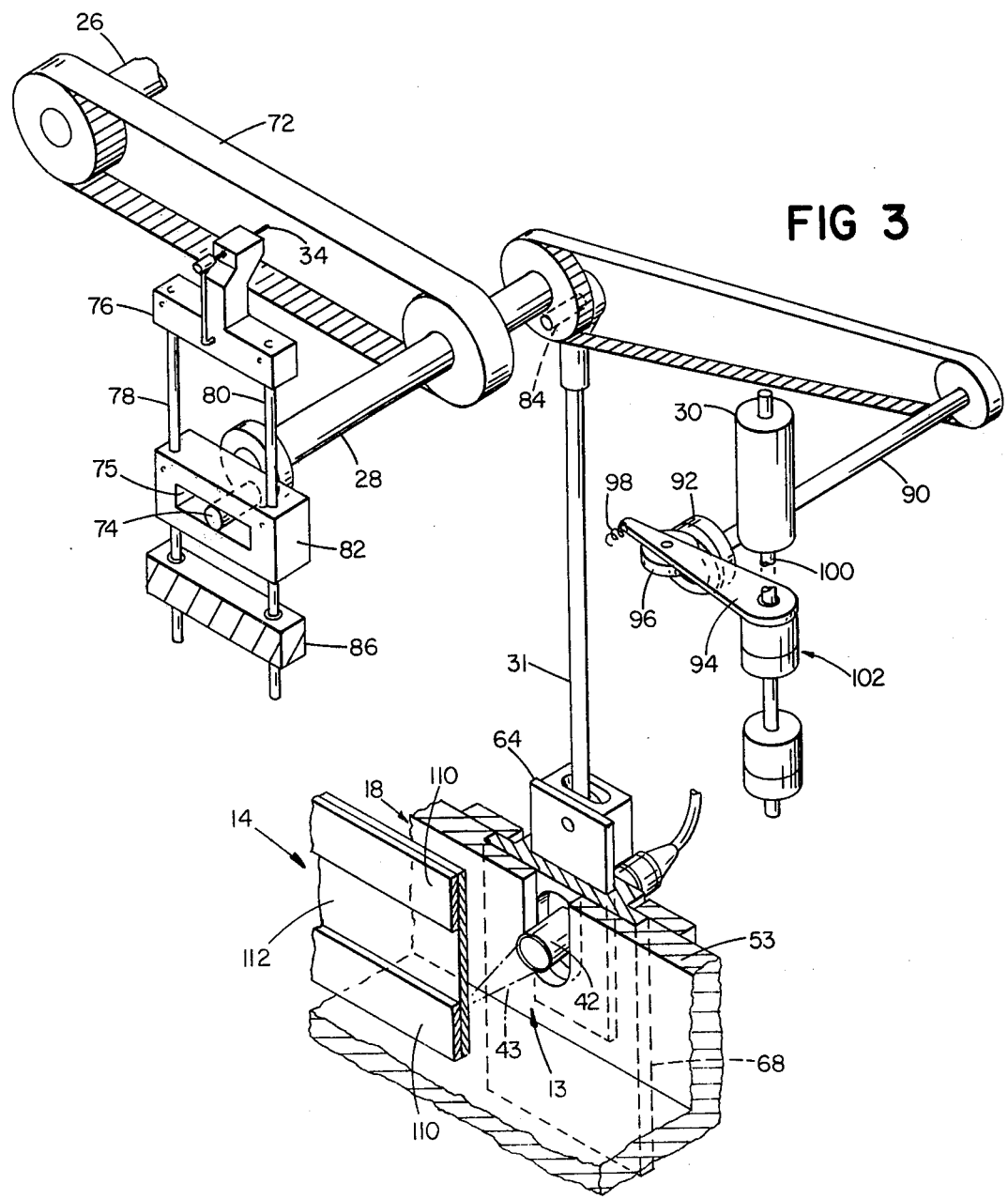
FIG. 3 shows portions of the drive mechanism of the invention associated with timing functions.

Referring now to FIG. 3, portions of the drive mechanism related to timing functions of the apparatus are seen.

Drive shaft 26 is driven by motor 11 (FIG. 1), and by means of a suitable chain or belt 72 drives crankshaft 28. A crank 74 is rotated at the forward end of crankshaft 28. Pen 34 is supported in structure 76, connected by rods 78 and 80 to block 82, which provides slot 75. Rods 78 and 80 are vertically slidable in suitable guide structure, indicated schematically by block 86 but not otherwise shown in the Figures. Crank 74 extends through slot 75. As crank 74 is revolved by crankshaft 28, it reciprocates block 82, carrying pen support structure 76, and thereby reciprocates pen 34.

A second crank 84 is rotated at the rear end of crankshaft 28. Connecting rod 31 is attached to crank 84 and supports transducer 42, which is reciprocated in phase with pen 34. The reciprocation of transducer 42 will be described more particularly in connection with FIG. 4.

Figure 2:
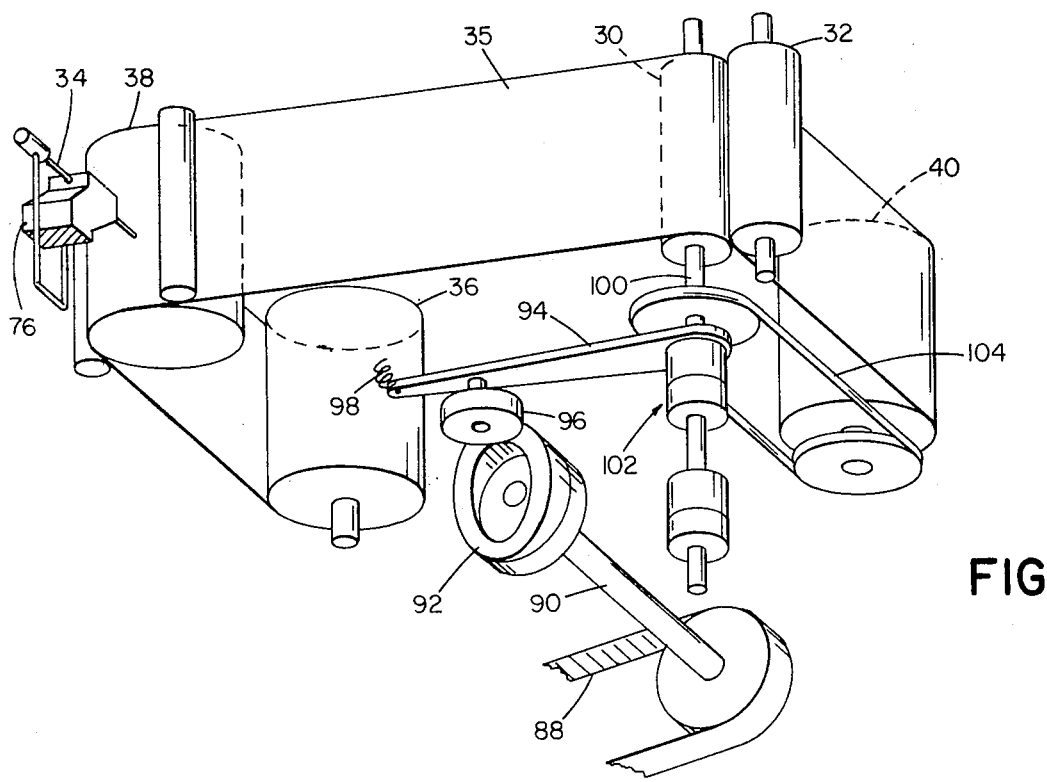
FIG. 2 is a view from below of the recording portion of the apparatus of the invention.

Still referring to FIG. 3, and also to FIG. 2, a belt 88 driven by crankshaft 28 drives shaft 90, which carries a cam 92. A cam operated lever arm 94 carries a cam follower 96, and is biassed by biassing means indicated schematically at 98 to hold follower 96 against cam 92. Lever arm 94 pivots about the vertical shaft 100 of driven pinch roll 30, and operates an indexing clutch 102. An O-ring 104 (FIG. 2), acting as a slip clutch, is driven by shaft 100, and drives paper takeup roll 40. When clutch 102 is engaged, pinch roll 30 is rotated through a small angular increment, and takeup roll 40 is also advanced through an angular increment. The second pinch roll 32 is free running, and is biassed (by conventional means, not shown) to nip paper strip 35 against driven roll 30. Cam 92 is set so that paper 35 is advanced between each two vertical strokes of pen 34. Preferably, the paper is advanced 0.030 inch per crankshaft revolution, or 0.015 inch after each pen stroke. The maximum spacing that gives a useful display is about 0.025 inch between pen strokes.

Figure 4:
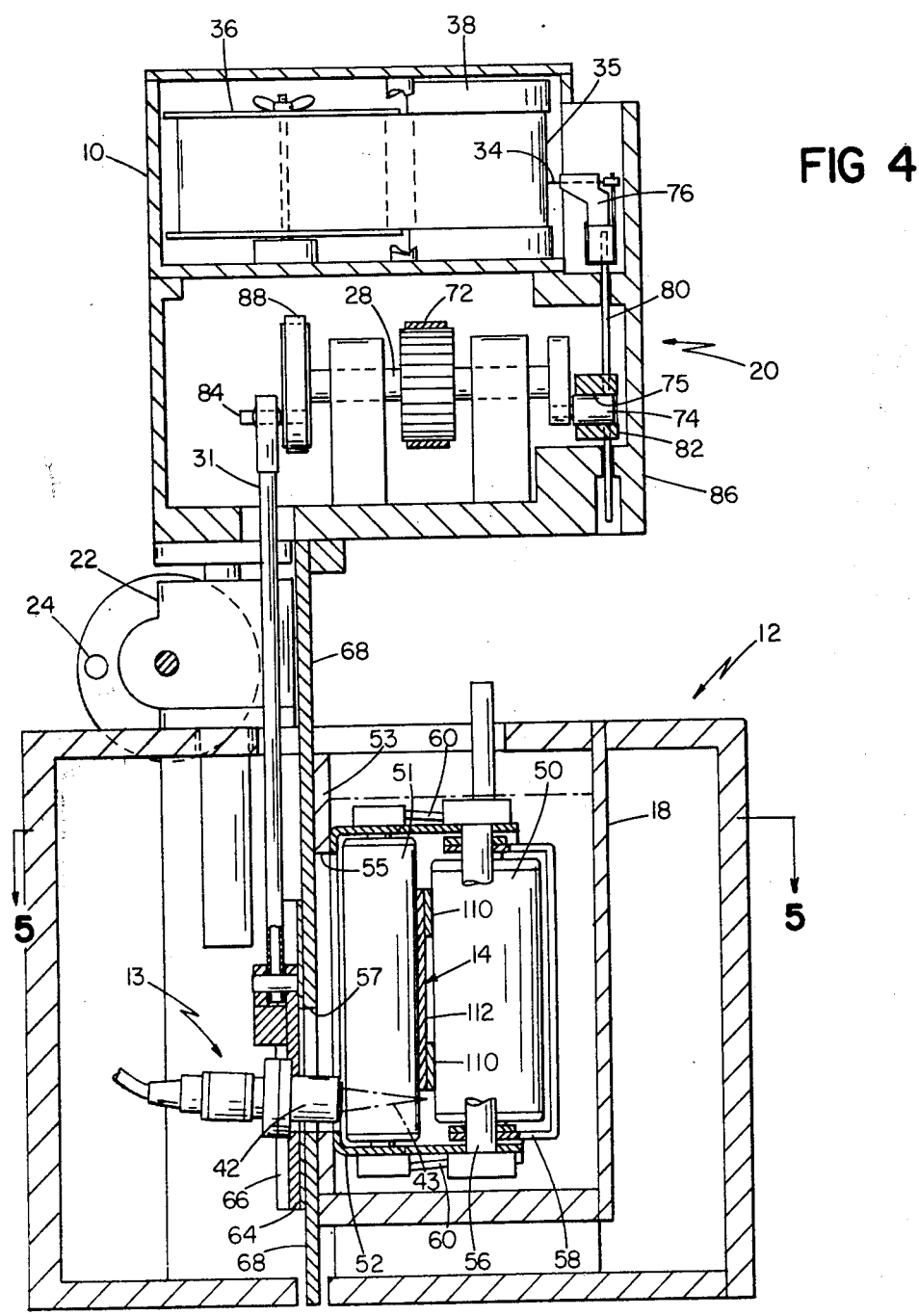
FIG. 4 is a section taken on lines 4—4 of FIG. 1.
Figure 5:
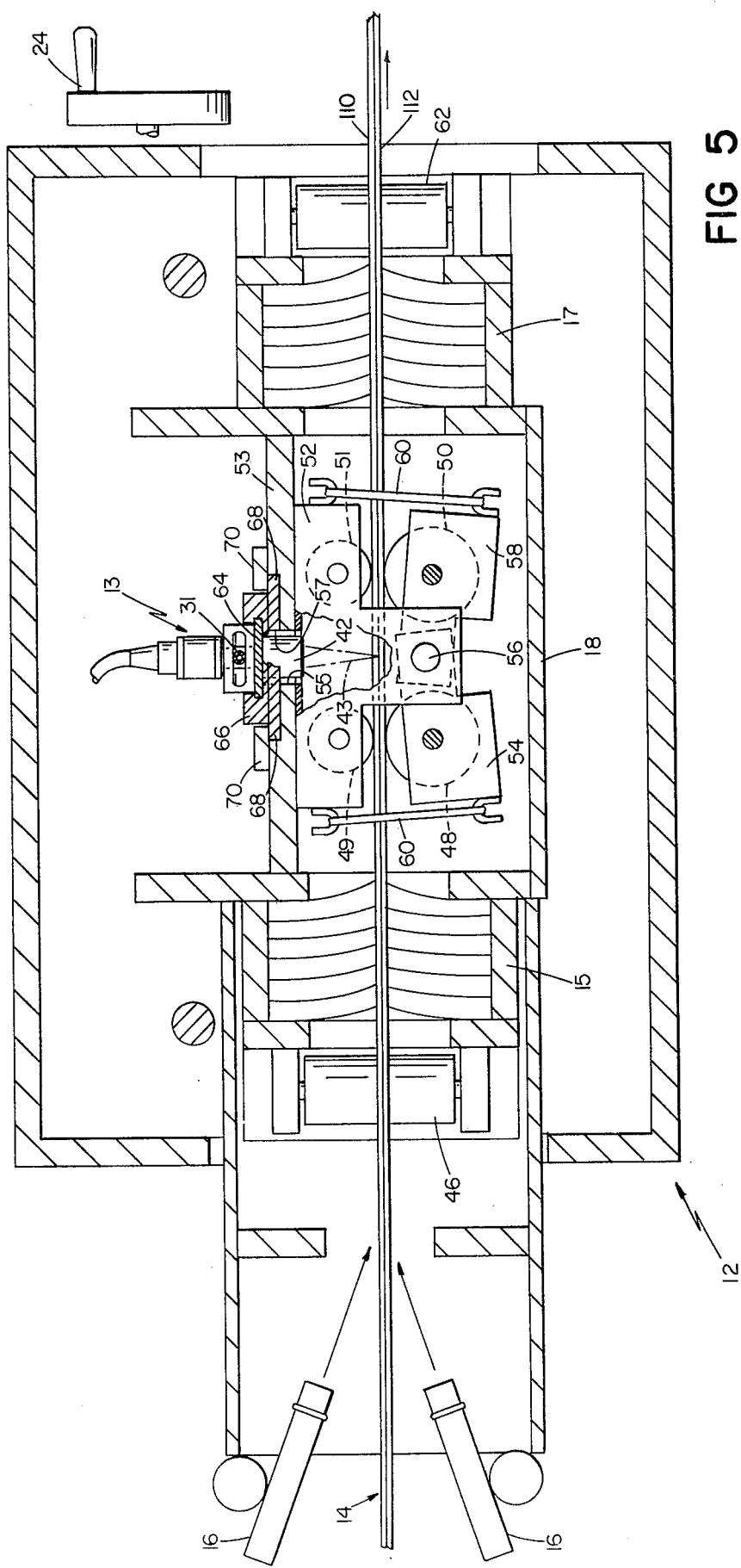
FIG. 5 is a section taken on lines 5—5 of FIG. 4.

Referring now to FIGS. 4 and 5, the interior of tank housing 12 is seen in more detail. Water tank 18 is open at its top surface to permit addition of water and to make possible the initial threading of the end of the workpiece to be scanned. Back wall 53 of tank 18 provides a scanning window 55.

Referring particularly to FIG. 5, the means defining the path of workpiece 14 through the apparatus of the invention will be described. Workpiece 14 enters tank housing 12 over a support roller 46 and passes through first stuffing box 15 into water tank 18. Within tank 18, workpiece 14 passes between a first pair of pinch rolls 48, 49 and a second pair of pinch rolls 50, 51. Rolls 49 and 51 are mounted on a support structure 52 which is fixed to tank back wall 53. Roll 48 is mounted on a support element 54 pivotable at a knuckle 56 on support element 52, and roll 50 is mounted on a similar support element 58. Pivotable support elements 54 and 58 are connected through tension elements 60 to fixed support structure 52. Rolls 48, 49 and 50, 51 maintain workpiece 14 in the focal plane of transducer 42 and generally on a level with scanning window 55 in back wall 53. Workpiece 14 passes through second stuffing box 17 and exits over a second support roller 62.

Referring now to FIG. 4, scanning unit 13 will be described in more detail. A vertical adjustment plate 68 is slidably retained within vertical guides 70 secured to the outer surface of tank back wall 53. A sliding seal is provided between plate 68 and wall 53. Vertical adjustment plate 68 is secured to upper housing 20 (FIGS. 1 and 4) and therefore is moved vertically together with housing 20 by means of jack 22. Vertical adjustment plate 68 covers scanning window 55 in any vertical position of the plate, and provides an outer window 57, having the same width as scanning window 55 but not as long. Outer window 57 overlies some portion of scanning window 55, the particular portion being determined by the vertical position of plate 68.

Transducer 42 is supported in a transducer plate 86 which is suspended from connecting rod 31, connected to crankshaft 28 (FIG. 1). The maximum crankshaft speed is about 286 r.p.m., giving a maximum rate of vertical travel of the transducer of 15 inches/second. Plate 64 is slidably retained within two vertical guides 66 secured to the outer surface of plate 68. A sliding seal is provided between plate 64 and plate 68. Transducer plate 64 is reciprocated within guides 66 by the motion of connecting rod 31, and has a sweep of about one inch. (Typically the bonded region is about ¾ inch wide). Transducer 42 extends into water tank 18 through outer window 57 and scanning window 55.

The particular one-inch vertical region of workpiece 14 that is scanned by transducer 42 is determined by the vertical adjustment of housing 20, carrying plate 68 with it, which in turn carries transducer 42. By this means the apparatus can scan a strip of silver up to one inch wide bonded to any region of the base. When two strips of silver are bonded in parallel to the base, the strips must be scanned alternately.

According to the invention, the method of in-line inspection of the moving workpiece can be employed, using the apparatus described herein. A sequence of ultrasonic signals is focussed on workpiece 14, using transducer 42. By reciprocation of transducer 42, the focus of the signals is reciprocated in the plane of the workpiece in a sweep transverse to the direction of travel of the workpiece. The sweep is at least commensurate with the width of the bonded region, about one inch. The signals reflected from the workpiece are received by transducer 42 and are processed by signal processor 44 to derive control signals, which are input to pen 34. Pen 34 is reciprocated in phase with the reciprocation of transducer 42. Paper strip 35 is moved past pen 34 transversely to the reciprocation of the pen, at a speed not greater than one-half the speed of travel of workpiece 14. In preferred methods, the workpiece may move ten times as fast as the paper. The resulting display, marked on paper strip 35, gives a useful representation of the characteristics of the bonded region of the workpiece.

In operation, the apparatus of the invention is connected in line with brazing apparatus, not shown, and workpiece 14 is threaded through water tank 18 to the takeup means, not shown. The speed of workpiece 14 as produced by the brazing apparatus is generally in the range from two to fifteen feet per minute, and typically about ten feet per minute. Preferably, the pen strokes drawn by reciprocating pen 34 on paper strip 35 are spaced at about one-tenth the distance of the scanned lines. For example, if the scanned lines are spaced apart by about 0.1 inch to 0.25 inch (when the workpiece travels at five to twelve feet/minute), the pen strokes are desirably spaced about 0.010 inch to 0.015 inch. This spacing gives a satisfactory statistical scan of the interface, and has been found to provide a useful representation of the type and characteristics of the void pattern. A pen stroke spacing of about 0.025 inch is the maximum that can be employed to give a useful display.

Figure 6:
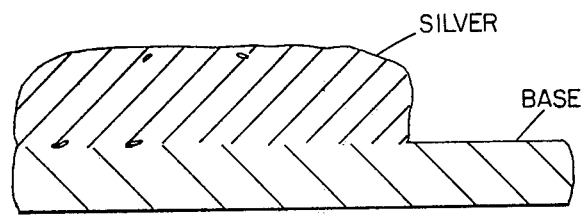
FIG. 6 is a tracing of a photomicrograph of a cross-section of a contact, made from a composite strip with a good bond, after extensive use.
Figure 7:
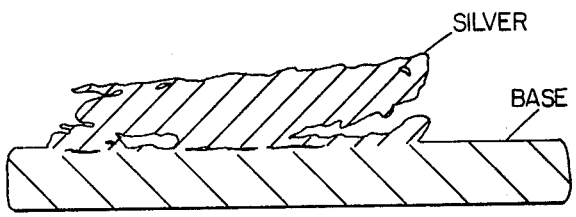
FIG. 7 is a tracing of a photomicrograph of a cross-section of a contact, made from a composite strip with a poor bond, after similar extensive use.

FIGS. 6 and 7 show tracings of photomicrographs of cross sections of contacts made from well bonded (FIG. 7) and badly bonded (FIG. 8) composite strips after extensive use. As is seen, the contact made with the bad bond has beenn badly eroded and the contact tip has actually been displaced from its original position on the base, while the contact made with the good bond shows only slight erosion. The importance of being able to control the production of the composite strip on-line, to minimize scrap and to increase the reliability of the manufactured contacts, is emphasized by these Figures.

What is claimed is:

1. Method of in line ultrasonic inspection of linearly extending brazed composite workpiece including a linearly extending bonded region, traveling linearly at a given speed, comprising the steps of
focussing a sequence of ultrasonic signals on said workpiece
reciprocating the focus of said signals in the plane of said workpiece in a sweep transverse to the direction of travel of said workpiece, said sweep being at least commensurate with the width of said bonded region,
receiving signals reflected from said workpiece
processing said received signals to derive control signals therefrom
inputting said control signals to a marker
reciprocating said marker in phase with the reciprocation of said focus
moving a linearly extending record medium past said marker transversely to the reciprocation of said marker at a speed not greater than one-half said workpiece given speed, whereby said marker traces successive generally parallel strokes against said record medium.

2. The method of claim 1, further including the step of moving said record medium past said marker intermittently, holding said medium at rest during each reciprocating stroke of said marker.

3. For in-line use with brazing apparatus producing a linearly extending brazed composite workpiece including a linearly extending bonded region, and moving linearly at a given speed, ultrasonic workpiece inspection apparatus comprising
guide means defining a workpiece path through said apparatus,
scanning means comprising
a transducer for emitting ultrasonic signals toward the workpiece and focussed on said workpiece path, and for receiving reflected ultrasonic signals therefrom,
first reciprocating means for reciprocating said transducer in a linear sweep path in the plane of said workpiece path and transverse to the direction of motion of the workpiece,
display means comprising
a linearly extending record medium,
a marker,
record medium advance means for advancing said record medium with respect to said marker at a speed not greater than one-half the workpiece given speed,
second reciprocating means for reciprocating said marker in the plane of said record medium and transverse to the advance of said record medium, whereby said marker moves in successive generally parallel strokes against said record medium,
actuating means for actuating said first and second reciprocating means in synchronism, and
signal processing means connected between said transducer and said marker for processing received reflected signals and for controlling said marker in accordance therewith to mark said record medium during said strokes.

4. The inspection apparatus of claim 3, wherein said sweep path is at least commensurate with the width of said bonded region.

5. The inspection apparatus of claim 3, wherein said record medium advance means is connected to said actuating means, and provides record medium takeup means and intermittent drive means connected to said takeup means, whereby said record medium is advanced between successive parallel strokes of said marker and is at rest during said strokes.

6. The in-line inspection apparatus of claim 2, wherein said record medium advance speed is such that said successive parallel strokes of said marker on said record medium are spaced apart by not more than 0.025 inch.

* * * * *